US008167856B2

(12) United States Patent
Kazala, Jr. et al.

(10) Patent No.: US 8,167,856 B2
(45) Date of Patent: May 1, 2012

(54) INFLATABLE BLADDER DRESSINGS, SYSTEMS, AND METHODS

(75) Inventors: Richard Marvin Kazala, Jr., San Antonio, TX (US); Justin Alexander Long, San Antonio, TX (US); Robert Peyton Wilkes, San Antonio, TX (US); Carrie Ann Kauffman, San Antonio, TX (US)

(73) Assignee: KCI Licensing, Inc, San Antonio, TX (US)

( * ) Notice: Subject to any disclaimer, the term of this patent is extended or adjusted under 35 U.S.C. 154(b) by 268 days.

(21) Appl. No.: 12/475,373

(22) Filed: May 29, 2009

(65) Prior Publication Data

US 2009/0299308 A1    Dec. 3, 2009

Related U.S. Application Data

(60) Provisional application No. 61/057,807, filed on May 30, 2008, provisional application No. 61/057,798, filed on May 30, 2008, provisional application No. 61/057,808, filed on May 30, 2008, provisional application No. 61/057,802, filed on May 30, 2008, provisional application No. 61/057,800, filed on May 30, 2008, provisional application No. 61/057,797, filed on May 30, 2008, provisional application No. 61/057,805, filed on May 30, 2008, provisional application No. 61/057,810, filed on May 30, 2008, provisional application No. 61/121,362, filed on Dec. 10, 2008, provisional application No. 61/144,067, filed on Jan. 12, 2009, provisional application No. 61/057,803, filed on May 30, 2008.

(51) Int. Cl.
*A61M 1/00* (2006.01)

(52) U.S. Cl. .......................................... 604/313; 602/41
(58) Field of Classification Search .................. 604/313; 602/41–43, 46, 48, 52–54, 56
See application file for complete search history.

(56) References Cited

U.S. PATENT DOCUMENTS

| | | | |
|---|---|---|---|
| 1,195,430 | A | 8/1916 | Angier |
| 1,355,846 | A | 10/1920 | Rannells |
| 1,845,630 | A | 2/1932 | Scholl |
| 2,452,345 | A | 10/1948 | Anselmo |
| 2,547,758 | A | 4/1951 | Keeling |

(Continued)

FOREIGN PATENT DOCUMENTS

AU    550575 A1    8/1982

(Continued)

OTHER PUBLICATIONS

International Search Report and Written Opinion date mailed Feb. 25, 2010; PCT International Application No. PCT/US2009/045750.

(Continued)

*Primary Examiner* — Melanie Hand
(74) *Attorney, Agent, or Firm* — SNR Denton US LLP

(57) ABSTRACT

A system for providing reduced-pressure treatment to a tissue site of a patient includes a reduced-pressure source for supplying reduced pressure, a fluid source for supplying a fluid, and a plurality of inflatable bladders for placing adjacent the tissue site. The inflatable bladders are operable to receive the fluid to expand from an uninflated position to an inflated position. The system also includes a plurality of chambers that are compressible. At least one of the plurality of chambers is disposed between a first inflatable bladder and a second inflatable bladder of the plurality of inflatable bladders.

25 Claims, 7 Drawing Sheets

U.S. PATENT DOCUMENTS

| | | | |
|---|---|---|---|
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,026,874 A | 3/1962 | Stevens | |
| 3,066,672 A | 12/1962 | Crosby, Jr. et al. | |
| 3,367,332 A | 2/1968 | Groves | |
| 3,419,006 A | 12/1968 | King | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 3,892,229 A | 7/1975 | Taylor et al. | |
| 4,080,970 A | 3/1978 | Miller | |
| 4,091,804 A * | 5/1978 | Hasty | 601/152 |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,224,945 A * | 9/1980 | Cohen | 606/201 |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,266,545 A | 5/1981 | Moss | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,375,217 A | 3/1983 | Arkans | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A * | 8/1986 | Nielsen | 604/23 |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,722,332 A * | 2/1988 | Saggers | 602/62 |
| 4,727,868 A | 3/1988 | Szycher et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,770,490 A | 9/1988 | Gruenewald et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,902,565 A | 2/1990 | Brook | |
| 4,906,233 A | 3/1990 | Moriuchi et al. | |
| 4,906,240 A | 3/1990 | Reed et al. | |
| 4,917,112 A | 4/1990 | Kalt | |
| 4,919,654 A | 4/1990 | Kalt et al. | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,000,741 A | 3/1991 | Kalt | |
| 5,018,515 A | 5/1991 | Gilman | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,106,629 A | 4/1992 | Cartmell et al. | |
| 5,134,994 A | 8/1992 | Say | |
| 5,149,331 A | 9/1992 | Ferdman et al. | |
| 5,160,315 A | 11/1992 | Heinecke et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,380,294 A | 1/1995 | Persson | |
| 5,423,737 A | 6/1995 | Cartmell et al. | |
| 5,429,593 A | 7/1995 | Matory | |
| 5,435,009 A | 7/1995 | Schild et al. | |
| 5,437,622 A | 8/1995 | Carion | |
| 5,437,651 A | 8/1995 | Todd et al. | |
| 5,489,262 A | 2/1996 | Cartmell et al. | |
| 5,497,788 A | 3/1996 | Inman et al. | |
| 5,520,629 A | 5/1996 | Heinecke et al. | |
| 5,527,293 A | 6/1996 | Zamierowski | |
| 5,538,502 A | 7/1996 | Johnstone | |
| 5,549,584 A | 8/1996 | Gross | |
| 5,556,375 A | 9/1996 | Ewall | |
| 5,607,388 A | 3/1997 | Ewall | |
| 5,628,230 A | 5/1997 | Flam | |
| 5,636,643 A | 6/1997 | Argenta et al. | |
| 5,645,081 A | 7/1997 | Argenta et al. | |
| 5,653,244 A | 8/1997 | Shaw | |
| 5,792,088 A | 8/1998 | Felder et al. | |
| 5,844,013 A | 12/1998 | Kenndoff et al. | |
| 5,866,249 A | 2/1999 | Yarusso et al. | |
| 5,950,238 A | 9/1999 | Klein | |
| 6,071,267 A | 6/2000 | Zamierowski | |
| 6,086,450 A | 7/2000 | Mankovitz | |
| 6,109,267 A | 8/2000 | Shaw et al. | |
| 6,135,116 A | 10/2000 | Vogel et al. | |
| 6,162,960 A | 12/2000 | Klein | |
| 6,213,840 B1 | 4/2001 | Han | |
| 6,241,747 B1 | 6/2001 | Ruff | |
| 6,270,910 B1 | 8/2001 | Jaeger et al. | |
| 6,287,316 B1 | 9/2001 | Agarwal et al. | |
| 6,345,623 B1 | 2/2002 | Heaton et al. | |
| 6,361,397 B1 | 3/2002 | Mankovitz et al. | |
| 6,420,622 B1 | 7/2002 | Johnston et al. | |
| 6,440,093 B1 | 8/2002 | McEwen et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,648,862 B2 | 11/2003 | Watson | |
| 6,685,681 B2 | 2/2004 | Lockwood et al. | |
| 6,752,794 B2 | 6/2004 | Lockwood et al. | |
| 6,814,079 B2 | 11/2004 | Heaton et al. | |
| 6,824,533 B2 | 11/2004 | Risk, Jr. et al. | |
| 6,855,135 B2 | 2/2005 | Lockwood et al. | |
| 6,867,342 B2 | 3/2005 | Johnston et al. | |
| D503,509 S | 4/2005 | Bell et al. | |
| 6,936,037 B2 | 8/2005 | Bubb et al. | |
| 6,951,553 B2 | 10/2005 | Bubb et al. | |
| 7,004,915 B2 | 2/2006 | Boynton et al. | |
| 7,070,584 B2 | 7/2006 | Johnson et al. | |
| 7,090,647 B2 | 8/2006 | Mimura et al. | |
| 7,135,007 B2 | 11/2006 | Scott et al. | |
| 7,144,294 B2 | 12/2006 | Bell et al. | |
| 7,195,624 B2 | 3/2007 | Lockwood et al. | |
| 7,201,063 B2 | 4/2007 | Taylor | |
| 7,201,263 B2 | 4/2007 | Osada et al. | |
| 7,214,202 B1 * | 5/2007 | Vogel et al. | 601/11 |
| 7,316,672 B1 | 1/2008 | Hunt et al. | |
| 7,361,184 B2 | 4/2008 | Joshi | |
| 7,455,681 B2 | 11/2008 | Wilke et al. | |
| 7,504,549 B2 | 3/2009 | Castellani et al. | |

| | | |
|---|---|---|
| 7,520,872 B2 | 4/2009 | Biggie et al. |
| 7,532,953 B2 | 5/2009 | Vogel |
| 7,569,742 B2 | 8/2009 | Haggstrom |
| 7,699,831 B2 | 4/2010 | Bengtson et al. |
| 2001/0029956 A1 | 10/2001 | Argenta et al. |
| 2001/0043943 A1 | 11/2001 | Coffey |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2003/0040691 A1 | 2/2003 | Griesbach et al. |
| 2003/0109816 A1 | 6/2003 | Lachenbruch et al. |
| 2003/0212359 A1 | 11/2003 | Butler |
| 2004/0039415 A1 | 2/2004 | Zamierowski |
| 2004/0064111 A1 | 4/2004 | Lockwood et al. |
| 2004/0064132 A1 | 4/2004 | Boehringer et al. |
| 2004/0242119 A1 | 12/2004 | Francis |
| 2004/0243073 A1 | 12/2004 | Lockwood |
| 2005/0209574 A1 | 9/2005 | Boehringer et al. |
| 2005/0222544 A1 | 10/2005 | Weston |
| 2005/0228329 A1 | 10/2005 | Boehringer et al. |
| 2006/0041247 A1 | 2/2006 | Petrosenko et al. |
| 2006/0064049 A1 | 3/2006 | Marcussen |
| 2006/0079852 A1 | 4/2006 | Bubb et al. |
| 2006/0149171 A1 | 7/2006 | Vogel et al. |
| 2006/0173253 A1 | 8/2006 | Ganapathy |
| 2006/0189910 A1 | 8/2006 | Johnson et al. |
| 2006/0213527 A1 | 9/2006 | Argenta et al. |
| 2006/0264796 A1 | 11/2006 | Flick et al. |
| 2007/0021697 A1 | 1/2007 | Ginther |
| 2007/0027414 A1 | 2/2007 | Hoffman et al. |
| 2007/0066946 A1 | 3/2007 | Haggstrom et al. |
| 2007/0078366 A1 | 4/2007 | Haggstrom et al. |
| 2007/0135777 A1 | 6/2007 | Greene et al. |
| 2007/0185426 A1 | 8/2007 | Ambrosio et al. |
| 2007/0219497 A1 | 9/2007 | Johnson |
| 2007/0219513 A1 | 9/2007 | Lina et al. |
| 2007/0219532 A1 | 9/2007 | Karpowicz et al. |
| 2008/0004549 A1 | 1/2008 | Anderson et al. |
| 2008/0009812 A1 | 1/2008 | Riesinger |
| 2008/0039763 A1 | 2/2008 | Sigurjonsson et al. |
| 2008/0076844 A1 | 3/2008 | Van Sumeren et al. |
| 2009/0043268 A1 | 2/2009 | Eddy et al. |
| 2009/0177051 A1 | 7/2009 | Arons et al. |
| 2009/0204084 A1 | 8/2009 | Blott et al. |
| 2009/0204085 A1 | 8/2009 | Biggie et al. |
| 2009/0227968 A1 | 9/2009 | Vess |
| 2009/0234307 A1 | 9/2009 | Vitaris |
| 2009/0264807 A1 | 10/2009 | Haggstrom |
| 2009/0293887 A1 | 12/2009 | Wilkes et al. |

FOREIGN PATENT DOCUMENTS

| | | |
|---|---|---|
| AU | 745271 | 4/1999 |
| AU | 755496 | 2/2002 |
| CA | 2005436 | 6/1990 |
| DE | 26 40 413 A1 | 3/1978 |
| DE | 39 07 522 C1 | 4/1990 |
| DE | 43 06 478 A1 | 9/1994 |
| DE | 295 04 378 U1 | 10/1995 |
| DE | 20 2006 007877 | 7/2006 |
| DE | 10 2005 007016 A1 | 8/2006 |
| EP | 0100148 A1 | 2/1984 |
| EP | 0117632 A2 | 9/1984 |
| EP | 0161865 A2 | 11/1985 |
| EP | 0330373 A2 | 8/1989 |
| EP | 0358302 A2 | 3/1990 |
| EP | 0424165 A1 | 4/1991 |
| EP | 0691113 A1 | 1/1996 |
| EP | 1018967 B1 | 8/2004 |
| FR | 1163907 A | 10/1958 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 333 965 A | 8/1999 |
| GB | 2 329 127 B | 8/2000 |
| JP | 4129536 | 4/1992 |
| SG | 71559 | 4/2002 |
| WO | WO 80/02182 | 10/1980 |
| WO | WO 87/04626 | 8/1987 |
| WO | WO 90/10424 | 9/1990 |
| WO | WO 93/09727 | 5/1993 |
| WO | WO 94/20041 | 9/1994 |
| WO | WO 95/14451 A1 | 6/1995 |
| WO | WO-95/14451 A1 | 6/1995 |
| WO | WO 96/05873 | 2/1996 |
| WO | WO 97/18007 | 5/1997 |
| WO | WO 99/13793 | 3/1999 |
| WO | WO-00/07653 A1 | 2/2000 |
| WO | WO 00/07653 A1 | 2/2000 |
| WO | WO-03/057071 A2 | 7/2003 |
| WO | WO 03/057071 A2 | 7/2003 |
| WO | WO 03/057307 A1 | 7/2003 |
| WO | WO-03/057307 A1 | 7/2003 |
| WO | WO 03/086262 A2 | 10/2003 |
| WO | WO-03/086262 A2 | 10/2003 |
| WO | WO 2005123170 A1 | 12/2005 |
| WO | WO-2006/012745 A1 | 2/2006 |
| WO | WO 2006/012745 A1 | 2/2006 |
| WO | WO 2007/031762 | 3/2007 |
| WO | WO 2007/033679 | 3/2007 |
| WO | WO 2007/041642 A2 | 4/2007 |
| WO | WO 2008/054312 A1 | 5/2008 |
| WO | WO-2008/063281 A2 | 5/2008 |
| WO | WO 2008/063281 A2 | 5/2008 |
| WO | WO-2009/019496 A2 | 2/2009 |
| WO | WO 2009/019496 A2 | 2/2009 |
| WO | WO-2009/047524 A2 | 4/2009 |
| WO | WO 2009/047524 A2 | 4/2009 |
| WO | WO 2009/071926 A1 | 6/2009 |
| WO | WO-2009/071926 A1 | 6/2009 |

OTHER PUBLICATIONS

International Search Report and Written Opinion date mailed Mar. 12, 2010; PCT International Application No. PCT/US2009/045755.

N.A. Bagautdinov, "Variant of External Vacuum Aspiration in the Treatment of Purulent Diseases of the Soft Tissues," Current Problems in Modem Clinical Surgery: Interdepartmental Collection, edited by V. Ye Volkov et al. (Chuvashia State University, Cheboksary, U.S.S.R. 1986);pp. 94-96 (certified translation).

Louis C. Argenta, MD and Michael J. Morykwas, PhD; "Vacuum-Assisted Closure: A New Method for Wound Control and Treatment: Clinical Experience"; Annals of Plastic Surgery, vol. 38, No. 6, Jun. 1997; pp. 563-576.

Susan Mendez-Eastmen, RN; "When Wounds Won't Heal" RN Jan. 1998, vol. 61 (1); Medical Economics Company, Inc., Montvale, NJ, USA; pp. 20-24.

James H. Blackburn, II, MD, et al; "Negative-Pressure Dressings as a Bolster for Skin Grafts"; Annals of Plastic Surgery, vol. 40, No. 5, May 1998, pp. 453-457.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu. N., et al; "Active Wound Drainage", Vestnik Khirurgi, vol. 138, Issue 4, 1987, and 7 page English translation thereof.

Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.

Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.

K.F. Jeter, T.E. Tintle, and M. Chariker, "Managing Draining Wounds and Fistulae: New and Established Methods," *Chronic Wound Care*, edited by D. Krasner (Health Management Publications, Inc., King of Prussia, PA 1990), pp. 240-246.

G. Živadinović, V. Žukić, Đ. Maksimović, Đ. Radak, and P. Peška, "Vacuum Therapy in the Treatment of Peripheral Blood Vessels," *Timok Medical Journal* 11 (1986), pp. 161-164 (certified translation).

F.E. Johnson, "An Improved Technique for Skin Graft Placement Using a Suction Drain," *Surgery, Gynecology, and Obstetrics* 159 (1984), pp. 584-585.

A.A. Safronov, Dissertation Abstract, *Vacuum Therapy of Trophic Ulcers of the Lower Leg with Simultaneous Autoplasty of the Skin* (Central Scientific Research Institute of Traumatology and Orthopedics, Moscow, U.S.S.R. 1967) (certified translation).

M. Schein, R. Saadia, J.R. Jamieson, and G.A.G. Decker, "The 'Sandwich Technique' in the Management of the Open Abdomen," *British Journal of Surgery* 73 (1986), pp. 369-370.

D.E. Tribble, An Improved Sump Drain-Irrigation Device of Simple Construction, *Archives of Surgery* 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," *Annals of Plastic Surgery* 38 (1997), pp. 553-562 (Morykwas I).

C.E. Tennants, "The Use of Hypermia in the Postoperative Treatment of Lesions of the Extremities and Thorax," *Journal of the American Medical Association* 64 (1915), pp. 1548-1549.

Selections from W. Meyer and V. Schmieden, *Bier's Hyperemic Treatment in Surgery, Medicine, and the Specialties: A Manual of Its Practical Application*, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

Laskin, et al.; "Minimally Invasive Total Knee Replacement Through a Mini-Midvastus Incision: An Outcome Study," Surgical Technology International XIII, 2004; 231-8.

A. Dee, "The successful management of a dehisced surgical wound with TNP following Femoropopliteal bypass", Journal of Wound Care, vol. 16, No. 1, Jan. 2007.

Ogazon, Use of Vacuum-Assisted Closure in the Treatment of Surgical Infection Sites Cir. Mar.-Apr. 2006; 74(2): 107-13 (Spanish).

Timmenga, "The Effects of Mechanical Stress on Healing Skin Wounds: An Experimental Study in Rabbits Using Tissues Expansions," British Journal of Plastic Surgery 1991; 44(7): 514-519.

Cunningham "Development of in-vitro Model to Simulate Dermal Wound Bed Interaction with GranuFoam and Gauze Dressing under Sub Atmospheric Pressure" RPT 111-05-02, Device Implant Innovations 2006.

Delalleau, A., et al, "Characterization of the Mechanical Properties of Skin by Inverse Analysis Combined with the Indentation Test" Journal of Biomechanics, 2006; pp. 1603-1610.

Pailler-Mattei, C., "Caracte; Risation Me' Canique et Tribologizue de la Peau Humain In Vivo", 2004-31.

Khatyr, F., "Model of the Viscoelastic Behavior of Skin In Vivo and Study of Anisotropy", Skin Research and Technology 2004; pp. 96-103.

Wilkes, "3D Strain Measurement in Soft Tissue: Demonstration of a Novel Inverse Finite Element Model Algorithm on MicroCT Images of a Tissue Phantom Exposed to Negative Pressure Wound Therapy," Journal of the Mechanical Behavior of Biomedical Materials (2008), pp. 1-16.

Diridollou, "In vivo Model of the Mechanical Properties of the Human Skin under Suction", Skin Research and Technology, 2000; 6:214-221.

Woo, "Structural Model to Describe the Non-Linear Stress-Strain Behavior for Parallel-Fibered Collagenous Tissues," Journal of Biomechanical Engineering, Nov. 1989, vol. 111/361.

International Search Report and Written Opinion date mailed Oct. 20, 2009; PCT International Application No. PCT/US2009/045747.

International Search Report and Written Opinion date mailed Oct. 16, 2009; PCT International Application No. PCT/US2009/045752.

Partial International Search Report and Written Opinion date mailed Oct. 7, 2009; PCT International Application No. PCT/US2009/045755.

International Search Report and Written Opinion date mailed Oct. 26, 2009; PCT International Application No. PCT/US2009/045751.

International Search Report and Written Opinion date mailed Oct. 14, 2009; PCT International Application No. PCT/US2009/045746.

International Search Report and Written Opinion date mailed Oct. 27, 2009; PCT International Application No. PCT/US2009/045744.

Partial International Search Report and Written Opinion date mailed Oct. 19, 2009; PCT International Application No. PCT/US2009/045742.

Partial Search Report date mailed Nov. 2, 2009; PCT International Application No. PCT/US2009/045750.

International Search Report and Written Opinion date mailed Nov. 11, 2009; PCT International Application No. PCT/US2009/045754.

International Search Report and Written Opinion date mailed Oct. 21, 2009; PCT International Application No. PCT/US2009/045749.

International Search Report and Written Opinion date mailed Dec. 11, 2009; PCT International Application No. PCT/US2009/045753.

Partial Search Report date mailed Oct. 7, 2009; PCT International Application No. PCT/US2009/045755.

International Search Report and Written Opinion date mailed Oct. 26, 2009; PCT International Application No. PCT/US2009/045746.

Partial Search Report date mailed Oct. 19, 2009; PCT International Application No. PCT/US2009/045742.
Product Information for OptSite™ dressing.
Non-Final Rejection mailed Jul. 20, 2011 for U.S. Appl. No. 12/475,301.
Restriction Requirement mailed Aug. 16, 2011 for U.S. Appl. No. 12/475,380.
Restriction Requirement mailed May 10, 2011 for U.S. Appl. No. 12/475,285.
Response to Restriction Requirement filed Jun. 7, 2011 for U.S. Appl. No. 12/475,285.
Non-Final Rejection mailed Aug. 19, 2011 for U.S. Appl. No. 12/475,285.
Restriction Requirement mailed May 10, 2011 for U.S. Appl. No. 12/475,367.
Response to Restriction Requirement filed Jun. 7, 2011 for U.S. Appl. No. 12/475,367.
Non-Final Rejection mailed Aug. 23, 2011 for U.S. Appl. No. 12/475,367.
Restriction Requirement mailed May 17, 2011 for U.S. Appl. No. 12/475,319.
Response to Restriction Requirement filed Jun. 7, 2011 for U.S. Appl. No. 12/475,319.
Non-Final Rejection mailed Aug. 18, 2011 for U.S. Appl. No. 12/475 319.
Non-Final Rejection mailed May 24, 2011 for U.S. Appl. No. 12/475,257.
Response to Non-Final Rejection filed Jul. 27, 2011 for U.S. Appl. No. 12/475,257.
Restriction Requirement mailed May 9, 2011 for U.S. Appl. No. 12/475,388.
Response to Restriction Requirement filed Jun. 7, 2011 for U.S. Appl. No. 12/475,388.
Non-Final Rejection mailed Sep. 7, 2011 for U.S. Appl. No. 12/475,388.
Restriction Requirement mailed Apr. 29, 2011 for U.S. Appl. No. 12/475,231.
Response to Restriction Requirement filed May 19, 2011 for U.S. Appl. No. 12/475,231.
Non-Final Rejection mailed Sep. 6, 2011 for U.S. Appl. No. 12/475,231.
Restriction Requirement mailed May 12, 2011 for U.S. Appl. No. 12/475,407.
Response to Restriction Requirement filed Jun. 7, 2011 for U.S. Appl. No. 12/475,407.
Non-Final Rejection mailed Aug. 23, 2011 for U.S. Appl. No. 12/475,407.
International Search Report and Written Opinion date mailed Aug. 30, 2011 for PCT International Application No. PCT/US2011/034300.
Response filed Oct. 20, 2011 for U.S. Appl. No. 12/475,285.
Interview Summary date mailed Oct. 26, 2011 for U.S. Appl. No. 12/475,285.
Response filed Sep. 13, 2011 for U.S. Appl. No. 12/475,380.
Non-Final Office Action date mailed Sep. 15, 2011 for U.S. Appl. No. 12/475,398.
Response filed Oct. 5, 2011 for U.S. Appl. No. 12/475,301.
Response filed Oct. 18, 2011 for U.S. Appl. No. 12/475,367.
Response filed Oct. 20, 2011 for U.S. Appl. No. 12/475,319.
Interview Summary date mailed Oct. 26, 2011 for U.S. Appl. No. 12/475,319.
Restriction Requirement date mailed Oct. 12, 2011 for U.S. Appl. No. 12/475,328.
Response filed Oct. 19, 2011 for U.S. Appl. No. 12/475,328.
Notice of Allowance date mailed Sep. 16, 2011 for U.S. Appl. No. 12/475,257.
Response filed Oct. 20, 2011 for U.S. Appl. No. 12/475,407.
Interview Summary date mailed Oct. 27, 2011 for U.S. Appl. No. 12/475,407.
Non-Final Office Action date mailed Dec. 28, 2011 for U.S. Appl. No. 12/475,285.
Non-Final Office Action date mailed Nov. 8, 2011 for U.S. Appl. No. 12/475,380.
Response filed Nov. 22, 2011 for U.S. Appl. No. 12/475,398.
Interview Summary date mailed Nov. 29, 2011 for U.S. Appl. No. 12/475,398.
Notice of Allowance date mailed Nov. 14, 2011 for U.S. Appl. No. 12/475,301.
Notice of Allowance date mailed Jan. 3, 2012 for U.S. Appl. No. 12/475,319.
Non-Final Office Action date mailed Dec. 9, 2011 for U.S. Appl. No. 12/475,328.
Response filed Nov. 11, 2011 for U.S. Appl. No. 12/475,388.
Interview Summary date mailed Dec. 5, 2011 for U.S. Appl. No. 12/475,388.
Response filed Nov. 11, 2011 for U.S. Appl. No. 12/475,231.
Interview Summary date mailed Dec. 5, 2011 for U.S. Appl. No. 12/475,231.
Notice of Allowance date mailed Jan. 9, 2012 for U.S. Appl. No. 12/475,407.

* cited by examiner

INFLATABLE BLADDER DRESSINGS, SYSTEMS, AND METHODS

RELATED APPLICATIONS

The present invention claims the benefit, under 35 USC §119(e), of the filing of U.S. Provisional Patent Application Ser. No. 61/057,807, entitled "Reduced-pressure Surgical Wound Treatment System," filed May 30, 2008; U.S. Provisional Patent Application Ser. No. 61/057,798, entitled "Dressing Assembly For Subcutaneous Wound treatment Using Reduce Pressure," filed May 30, 2008; U.S. Provisional Patent Application Ser. No. 61/057,808, entitled "See-Through, Reduced-Pressure Dressing," filed May 30, 2008; U.S. Provisional Patent Application Ser. No. 61/057,802, entitled "Reduced-Pressure Dressing Assembly For Use in Applying a Closing Force," filed May 30, 2008; U.S. Provisional Patent Application Ser. No. 61/057,803, entitled "Reduced-Pressure, Linear-Wound Treatment System," filed May 30, 2008; U.S. Provisional Patent Application Ser. No. 61/057,800, entitled "Reduced-Pressure, Compression System and Apparatus for use on a Curved Body Part," filed, May 30, 2008; U.S. Provisional Patent Application Ser. No. 61/057,797, entitled "Reduced-Pressure, Compression System and Apparatus for use on Breast Tissue," filed May 30, 2008; U.S. Provisional Patent Application Ser. No. 61/057,805, entitled "Super-Absorbent, Reduced-Pressure Wound Dressing and System," filed May 30, 2008; U.S. Provisional Patent Application Ser. No. 61/057,810, entitled "Reduced-Pressure, Compression System and Apparatus for use on a Joint," filed May 30, 2008; U.S. Provisional Patent Application Ser. No. 61/121,362, entitled "Reduced-Pressure Wound treatment System Employing an Anisotropic Drape," filed Dec. 10, 2008; and U.S. Provisional Patent Application Ser. No. 61/144,067, entitled "Reduced-Pressure, Compression System and Apparatus for use on a Joint," filed Jan. 12, 2009. All of these provisional applications are incorporated herein by reference for all purposes.

BACKGROUND

The present invention relates generally to medical treatment systems, and more particularly, to inflatable bladder dressings, systems, and methods.

Clinical studies and practice have shown that providing a reduced pressure in proximity to a tissue site augments and accelerates the growth of new tissue at the tissue site. The applications of this phenomenon are numerous, but application of reduced pressure has been particularly successful in treating wounds. This treatment (frequently referred to in the medical community as "negative pressure wound therapy," "reduced pressure therapy," or "vacuum therapy") provides a number of benefits, which may include faster healing and increased formulation of granulation tissue. Unless otherwise indicated, as used herein, "or" does not require mutual exclusivity. In addition, wounds may heal more quickly with additional care using other devices, such as sutures, staples, or other devices to help close the wound.

SUMMARY

According to an illustrative embodiment, a system for providing reduced-pressure treatment to a tissue site of a patient includes a reduced-pressure source for supplying reduced pressure, a fluid source for supplying a fluid, and a plurality of inflatable bladders for placing adjacent the tissue site. The inflatable bladders are operable to receive the fluid to expand from an un-inflated position to an inflated position. The system also includes a plurality of chambers that are compressible. At least one of the plurality of chambers is disposed between a first inflatable bladder and a second inflatable bladder of the plurality of inflatable bladders.

According to another illustrative embodiment, an apparatus includes a plurality of inflatable bladders for placing adjacent the tissue site. The inflatable bladders are operable to receive a fluid and to expand from an un-inflated position to an inflated position. The system also includes a plurality of chambers that are compressible. At least one of the plurality of chambers is disposed between a first inflatable bladder and a second inflatable bladder of the plurality of inflatable bladders.

According to another illustrative embodiment, a method for providing reduced-pressure treatment to a tissue site of a patient includes applying a multi-compartment dressing to the tissue site. The multi-compartment dressing includes a plurality of inflatable bladders for placing adjacent the tissue site. The inflatable bladders are operable to receive a fluid and to expand from an un-inflated position to an inflated position. The multi-compartment dressing also includes a plurality of chambers that are compressible. At least one of the plurality of chambers is disposed between a first inflatable bladder and a second inflatable bladder of the plurality of inflatable bladders. The chambers are compressed when the inflatable bladders expand to the inflated position or when reduced pressure is supplied to the chamber. The method also includes applying the fluid to the inflatable bladders to cause the inflatable bladders to expand into the inflated position, and applying a reduced pressure to the tissue site via the multi-compartment dressing.

According to another illustrative embodiment, a method of manufacturing includes the steps of forming a plurality of inflatable bladders and forming a plurality of chambers. The method further includes coupling the plurality of inflatable bladders and the plurality of chambers. The inflatable bladders are operable to receive a fluid and to expand from an un-inflated position to an inflated position.

DETAILED DESCRIPTION

Figure 1:
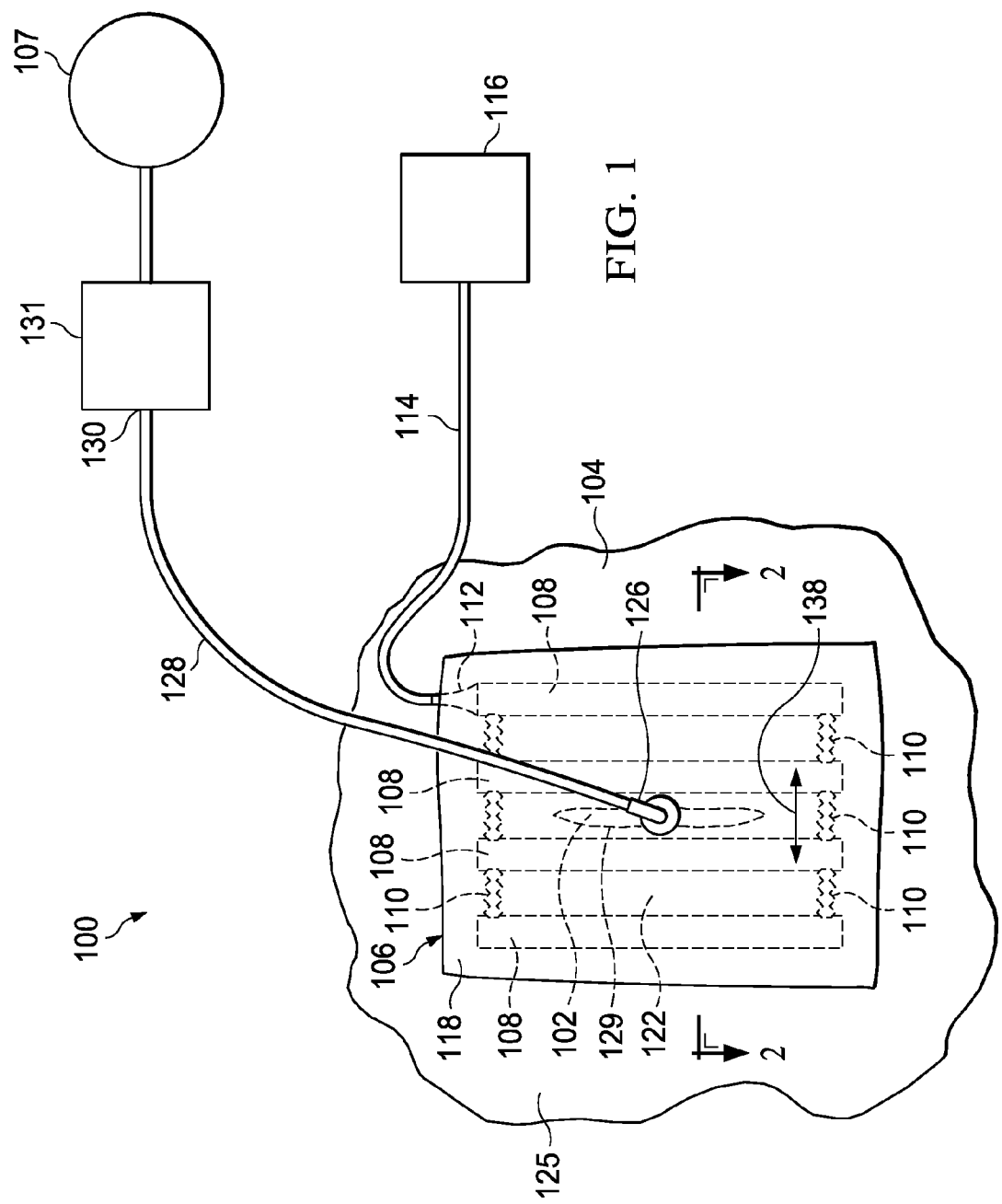
FIG. 1 is a schematic diagram, with a dressing shown from a top view, of a system for providing reduced-pressure treatment to a patient according to an illustrative embodiment.

In the following detailed description of the illustrative embodiments, reference is made to the accompanying drawings that form a part hereof. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments are defined only by the appended claims.

Referring now to FIGS. 1, 2A-2C, and 3, an illustrative embodiment of a system 100 for applying reduced-pressure treatment to a tissue site 102 of a patient 104 is shown. The reduced-pressure treatment may include reduced-pressure therapy or a reduced pressure generated closing force. The system 100 includes a multi-compartment dressing 106 to which reduced pressure is supplied from a reduced-pressure source 107 and a fluid may be supplied from a fluid supply 116.

The reduced-pressure source 107 may be any device for supplying a reduced pressure, such as a vacuum pump, wall suction, or other source. While the amount and nature of reduced pressure applied to a tissue site will typically vary according to the application, the reduced pressure will typically be between −5 mm Hg and −500 mm Hg and more typically between −100 mm Hg and −300 mm Hg.

As used herein, "reduced pressure" generally refers to a pressure less than the ambient pressure at a tissue site that is being subjected to treatment. In most cases, this reduced pressure will be less than the atmospheric pressure at which the patient is located. Alternatively, the reduced pressure may be less than a hydrostatic pressure at the tissue site. Unless otherwise indicated, values of pressure stated herein are gauge pressures. The reduced pressure delivered may be constant or varied (patterned or random) and may be delivered continuously or intermittently. Although the terms "vacuum" and "negative pressure" may be used to describe the pressure applied to the tissue site, the actual pressure applied to the tissue site may be more than the pressure normally associated with a complete vacuum. Consistent with the use herein, an increase in reduced pressure or vacuum pressure typically refers to a relative reduction in absolute pressure.

The multi-compartment dressing 106 includes inflatable bladders 108 that may be fluidly coupled to one another by one or more distribution conduits 110. The inflatable bladders 108 also include an interface 112 to which a fluid supply conduit 114 may be fluidly coupled so that fluid may be supplied to the inflatable bladders 108 by the fluid supply 116. As used herein, the term "coupled" includes coupling via a separate object and includes direct coupling. The term "coupled" also encompasses two or more components that are continuous with one another by virtue of each of the components being formed from the same piece of material. Also, the term "coupled" may include chemical, such as via a chemical bond, mechanical, thermal, or electrical coupling. Fluid coupling means that fluid is in communication between the designated parts or locations.

The multi-compartment dressing 106 also includes a drape 118 that covers the inflatable bladders 108 to form a plurality of chambers 120. A chamber 120 is disposed between each pair of the inflatable bladders 108. Thus, multiple compartments, e.g., inflatable bladders 108 and chambers 120, are formed. The drape 118, when covering the inflatable bladders 108 and sealed against the patient's epidermis 125 forms a sealed space 122 in which the inflatable bladders 108 are located. The drape 118 may be any material that provides a fluid seal. The drape 118 may, for example, be an impermeable or semi-permeable, elastomeric material. "Elastomeric" means having the properties of an elastomer. It generally refers to a polymeric material that has rubber-like properties. More specifically, most elastomers have elongation rates greater than 100% and a significant amount of resilience. The resilience of a material refers to the material's ability to recover from an elastic deformation. Examples of elastomers may include, but are not limited to, natural rubbers, polyisoprene, styrene butadiene rubber, chloroprene rubber, polybutadiene, nitrile rubber, butyl rubber, ethylene propylene rubber, ethylene propylene diene monomer, chlorosulfonated polyethylene, polysulfide rubber, polyurethane, EVA film, co-polyester, and silicones. Specific examples of drape 118 materials include a silicone drape, 3M Tegaderm® drape, acrylic drape such as one available from Avery Dennison, or an incise drape.

The sealing of the drape 118 to the patient's epidermis 125 is facilitated by an adhesive 124 that is disposed at the periphery of the inward, or tissue-facing, side of the drape 118. The adhesive 124 may be used to hold the drape 118 against the patient's epidermis 125 or another layer, such as a gasket or additional drape. The adhesive 124 may take numerous forms. For example, the adhesive 124 may be a medically acceptable, pressure-sensitive adhesive 124 that extends about a periphery of the drape 118.

The drape 118 also may include an aperture (not shown) into which a reduced-pressure interface 126 may be coupled. The reduced-pressure conduit 128 may be coupled to the reduced-pressure interface 126. Reduced pressure from the reduced-pressure source 107 may be transferred to the sealed space 122 via the reduced-pressure interface 126 and the reduced-pressure conduit 128. One function of the reduced pressure that is transferred to the multi-compartment dressing 106 is to provide reduced-pressure treatment to the tissue site 102.

The tissue site 102 may be the bodily tissue of any human, animal, or other organism, including bone tissue, adipose tissue, muscle tissue, dermal tissue, vascular tissue, connective tissue, cartilage, tendons, ligaments, or any other tissue. Treatment of tissue site 102 may include removal of fluids, e.g., ascites, exudate, or delivery of reduced pressure. The tissue site 102 may be or include a wound 129. The wound 129 on the tissue site 102 may be due to a variety of causes, including trauma, surgery, etc.

A medial portion 130 of reduced-pressure conduit 128 may have one or more devices, such as device 131. For example, the device 131 may be a fluid reservoir, or collection member to hold exudates and other fluids removed. Other examples of devices 131 that may be included on the medial portion 130 of reduced-pressure conduit 128 or otherwise fluidly coupled to the reduced-pressure conduit 128 include the following non-limiting examples: a pressure-feedback device, a volume detection system, a blood detection system, an infection detection system, a flow monitoring system, a temperature monitoring system, etc. Some of these devices may be formed integral to the reduced-pressure source 107. For example, a reduced-pressure port on the reduced-pressure source 107 may include a filter member that includes one or more filters, e.g., an odor filter. Also, the reduced-pressure conduit 128 and the fluid supply conduit 114 may be combined into a multi-lumen conduit having two or more lumens.

Any number of inflatable bladders 108 may be included in the multi-compartment dressing 106. The inflatable bladders 108 may be substantially parallel to one another. However, in other embodiments the inflatable bladders 108 may have a different orientation relative to one another. For example, the inflatable bladders 108 may have a radial configuration, wave pattern, etc. Also, the inflatable bladders 108 may be formed from any flexible material that allows the inflatable bladders 108 to expand and contract. For example, the inflatable bladders 108 may be formed from a soft polymer or any other flexible material.

Figure 2A:
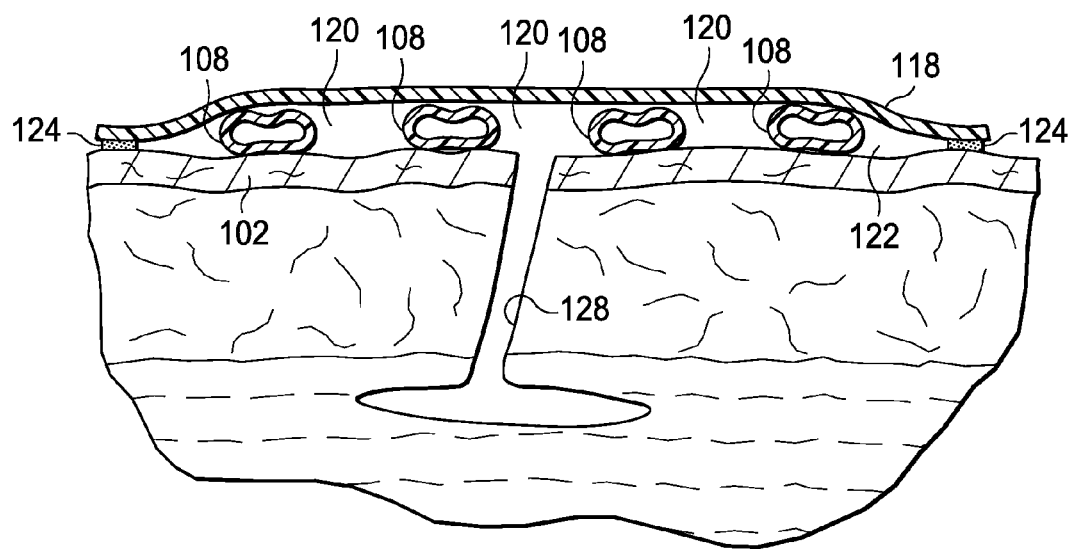
FIG. 2A is a schematic, cross-sectional view of the dressing shown in FIG. 1 having inflatable bladders in an un-inflated position.
Figure 2B:
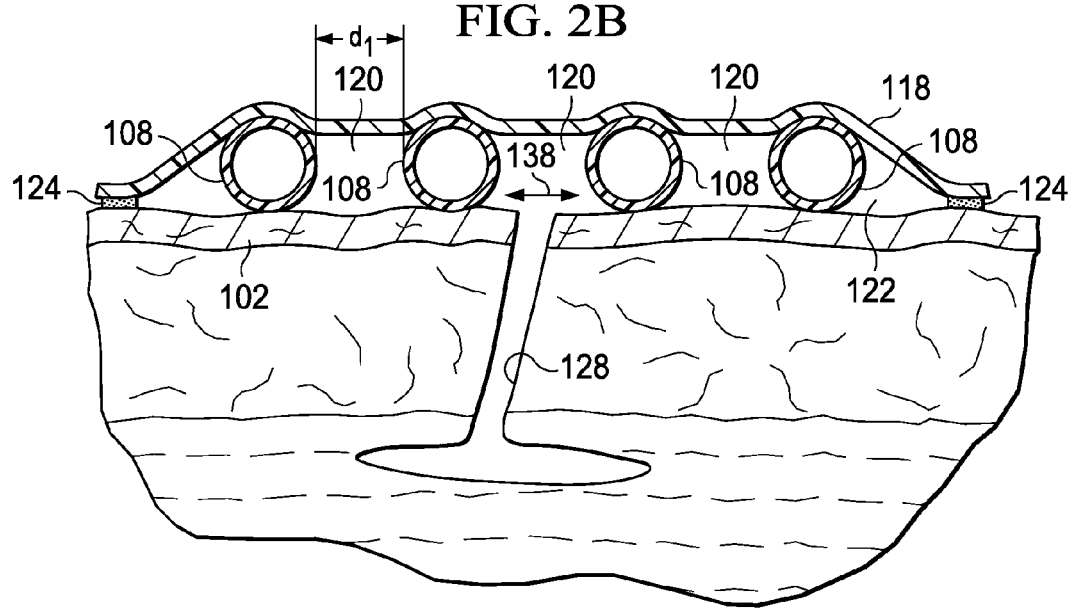
FIG. 2B is a schematic, cross-sectional view of the dressing shown in FIG. 1 having inflatable bladders in an inflated position.
Figure 2C:
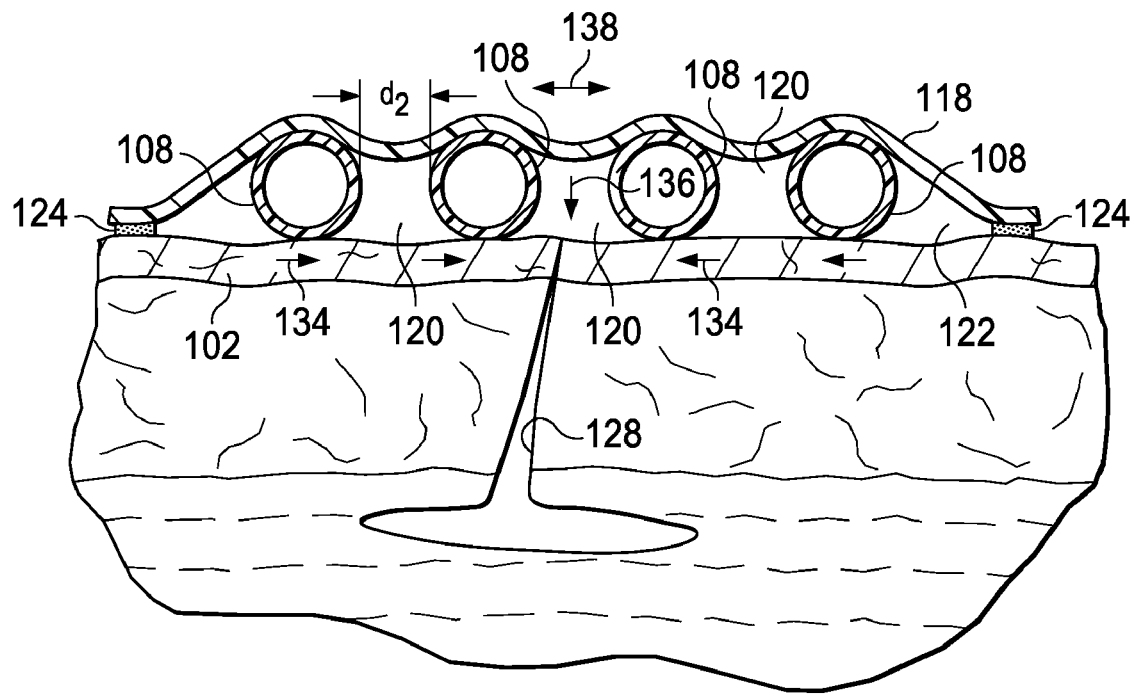
FIG. 2C is a schematic, cross-sectional view of the dressing shown in FIG. 1 having inflatable bladders in the inflated position and with reduced pressure applied to the chambers between the inflatable bladders.
Figure 3:
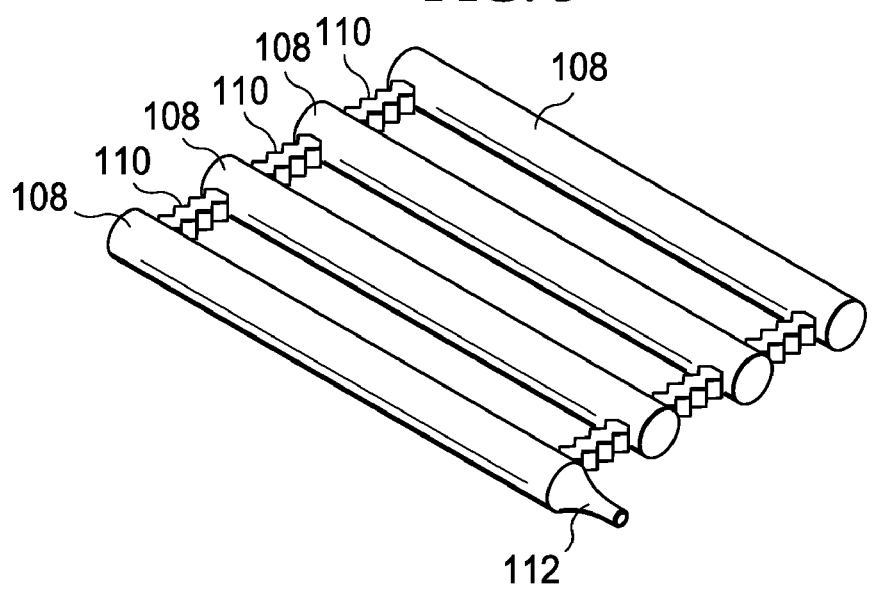
FIG. 3 is a schematic, perspective view of the inflatable bladders shown in FIG. 1.

Fluid may be supplied to the inflatable bladders 108 from the fluid supply 116 in order to inflate the inflatable bladders 108 from an un-inflated position to an inflated position. Reduced pressure may also be supplied to the chambers 120 to reduce the chambers' 120 volume or to provide reduced-pressure treatment to the tissue site 102. FIGS. 2A-2C show various states of the multi-compartment dressing 106 at different points in time. In FIG. 2A, the inflatable bladders 108 are in an un-inflated state and no reduced pressure is being applied to the chambers 120. In FIG. 2B, the inflatable bladders 108 are in an inflated position and reduced pressure is not yet being applied to the chambers 120. In FIG. 2C, the inflatable bladders 108 are in an inflated position and reduced pressure is being applied to the chambers 120, causing the chambers 120 to collapse and providing reduced-pressure treatment.

As shown in FIGS. 2B and 2C, the inflatable bladders 108 have a larger internal volume and a larger cross-section when in the inflated position. The distance between walls of adjacent inflatable bladders 108 may also decrease as the inflatable bladders 108 are filled with fluid from the fluid supply 116, thereby compressing the chambers 120. The volume of the chambers 120 may be further reduced by applying reduced pressure to the sealed space 122 under the drape 118. The chambers 120 are collapsible when such reduced pressure is applied from the reduced-pressure source 107 such that inflatable bladders 108 move closer to one another. Applying reduced pressure to the chambers 120 decreases the distance between the inflatable bladders 108. Thus, the distance is $d_1$ in the un-inflated portion shown in FIG. 2B and a distance $d_2$ in the inflated portion shown in FIG. 2C and $d_1 > d_2$.

With particular reference to FIG. 2C, the movement of the inflatable bladders 108 towards one another facilitates an inward, or closing, force 134 that can help to close or heal the wound 129. The inflation of the inflatable bladders 108 and the compression of the chambers 120 facilitate the overall compression of the multi-compartment dressing 106 along one direction, such as the direction indicated by bidirectional arrow 138. However, the multi-compartment dressing 106 may be compressed along two or more directions in other embodiments. The inflation of the inflatable bladders 108 may also help to create a compressive force 136 downward upon the tissue site 102.

The amount by which the inflatable bladders 108 are inflated and the amount of reduced pressure applied to the chambers 120 may be adjusted depending on the tissue site 102 being treated. For example, different magnitudes of the inward force 134 may be created by varying the amount of fluid supplied to the inflatable bladders 108 by the fluid supply 116. Likewise, the magnitude of the inward force 134 may be varied by adjusting the amount of reduced pressure that is applied to the chambers 120 by the reduced-pressure source 107. In addition to varying the reduced pressure and fluid applied to the multi-compartment dressing 106, the structure of the multi-compartment dressing 106 may also be modified for different treatment types. For example, the cross-sectional area, the cross-sectional shape, and the length of each of the inflatable bladders 108 can be modified from that shown in the figures. Also, the inflatable bladders 108 need not be uniform and may instead each have different structure and each receive different amounts of fluid, thus inflating the inflatable bladders to varying degrees. In similar fashion, the chambers 120 may each receive varying amounts of reduced pressure, thereby creating different compression forces 136 between each pair of the inflatable bladders 108.

The inward compression of the multi-compartment dressing 106, and in particular the compression of the inflatable bladders 108 toward one another, is facilitated by the corrugated structure of the distribution conduit 110 as shown clearly in FIG. 1. In particular, the corrugations in the distribution conduit 110 allow for the inflatable bladders to be compressed in an accordion-like manner. The distribution conduit 110 may be formed from any flexible material that facilitates the functions of the multi-compartment dressing 106.

A healthcare provider may implement treatment by applying the inflatable bladders 108 to the tissue site 102. The drape 118 may be applied over the inflatable bladders 108 such that the drape 118 covers the inflatable bladders 108. The reduced-pressure interface 126 is applied to the aperture in the drape 118. The conduits 128 and 114 may then be applied to the reduced-pressure interface 126 and the interface 112, respectively. Before, during, or after applying reduced pressure to the sealed space 122 by the reduced-pressure source 107, fluid may be supplied to the inflatable bladders 108 by the fluid supply 116. The application of both reduced pressure and fluid in this manner facilitates treatment of the tissue site 102.

In other embodiments, a third bladder or chamber (not shown) that is independently pressurized may be included in the multi-compartment dressing 106. Also, the chambers 120 may also receive positive pressure, instead of reduced pressure, to create an altered dressing structure. Although only a single layer of inflatable bladders 108 are shown, two or more layers of inflatable bladders 108 may be stacked atop one another in other embodiments. The walls of the inflatable bladders 108 may also include rigid structures, such as rigid, embedded plates, to alter the shape of the inflatable bladders 108 when in the inflated position. Fluids, including healing and growth factors that facilitate healing of the wound 129, may be introduced into the chambers 120 during reduced-pressure treatment. The fluid and reduced pressure levels that are supplied to the multi-compartment dressing 106 may be modulated over time to create dynamic loading of the tissue site 102. Such modulation may include pulsed or pressure wave rapid insufflations of air or other gas. Such modulation may also take place over the span of the multi-compartment dressing 106 to encourage directed interstitial fluid flow in the tissue site 102.

Figure 4A:
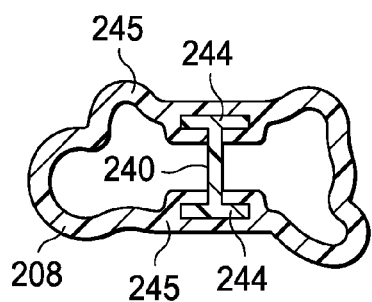
FIG. 4A is a schematic, cross-sectional view of an inflatable bladder having a strut and shown in the un-inflated position according to an illustrative embodiment.
Figure 4B:
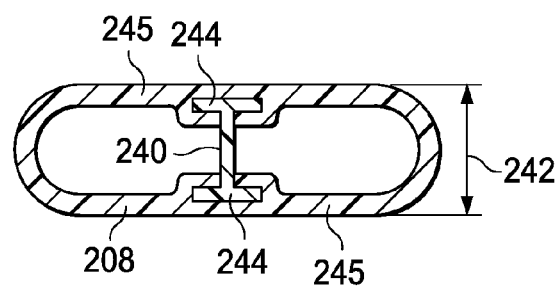
FIG. 4B is the inflatable bladder of FIG. 4A in the inflated position.

Referring now to FIGS. 4A and 4B, an inflatable bladder 208 is shown according to another illustrative embodiment. The inflatable bladder 208 may be used as part of a system for applying reduced-pressure treatment, such as the system 100 in FIGS. 1-3. The inflatable bladder 208 includes a strut 240 coupled to a wall 245 of the inflatable bladder 208. The strut 240 limits the expansion of the inflatable bladder along one direction, indicated by bidirectional arrow 242, when the inflatable bladder 208 is in the inflated position. The inflatable bladder 208 is shown in the un-inflated position in FIG. 4A, and in the inflated position in FIG. 4B. The strut 240 may be inserted in all or a portion of the inflatable bladder 208 located in the multi-compartment dressing 106. By limiting the expansion of the inflatable bladder 208, the compression and other forces applied to a tissue site may be customized to enhance tissue treatment.

The strut 240 may be any length and may be attached to the wall 245 of the inflatable bladder 208 in any manner. For example, the strut 240 may have flanges 244 on each end that are embedded in walls 245 of the inflatable bladder 208. In other embodiments, the strut 240 may be inserted in the inflatable bladder 208 in multiple orientations such that the inflatable bladder 208 is limited from expanding in two or more directions.

Figure 5:
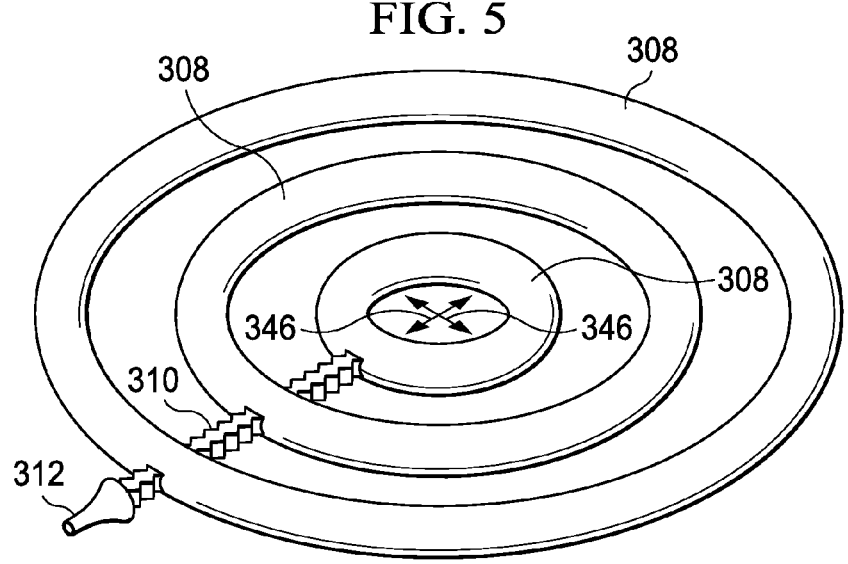
FIG. 5 is a schematic, perspective view of another illustrative embodiment of a portion of a system for providing reduced-pressure treatment.

Referring now to FIG. 5, another illustrative embodiment of inflatable bladders 308 is shown. In contrast to the inflatable bladders 108 shown in FIGS. 1 through 3, which have a substantially cylindrical shape when in the inflated position, each of the inflatable bladders 308 is a ring or annulus. The inflatable bladders 308 form concentric rings.

The inflatable bladders 308 are fluidly coupled to one another by a distribution conduit 310, which is corrugated to allow for movement of the inflatable bladders 308 towards one another. The distribution conduit 310 includes an interface 312 to which fluid may be applied via a supply fluid conduit. Like the inflatable bladders 108 in FIGS. 1 through 3, the inflatable bladders 308 shown in FIG. 5 may be covered by a drape to form a sealed space which comprises individual chambers between each pair of the inflatable bladders 308. The use of annular inflatable bladders 308 can facilitate particular compression and healing characteristics at a tissue site to which the inflatable bladders 308 are applied. For example, the inflatable bladders 308 may be compressible along multiple radial directions 346.

Figure 6:
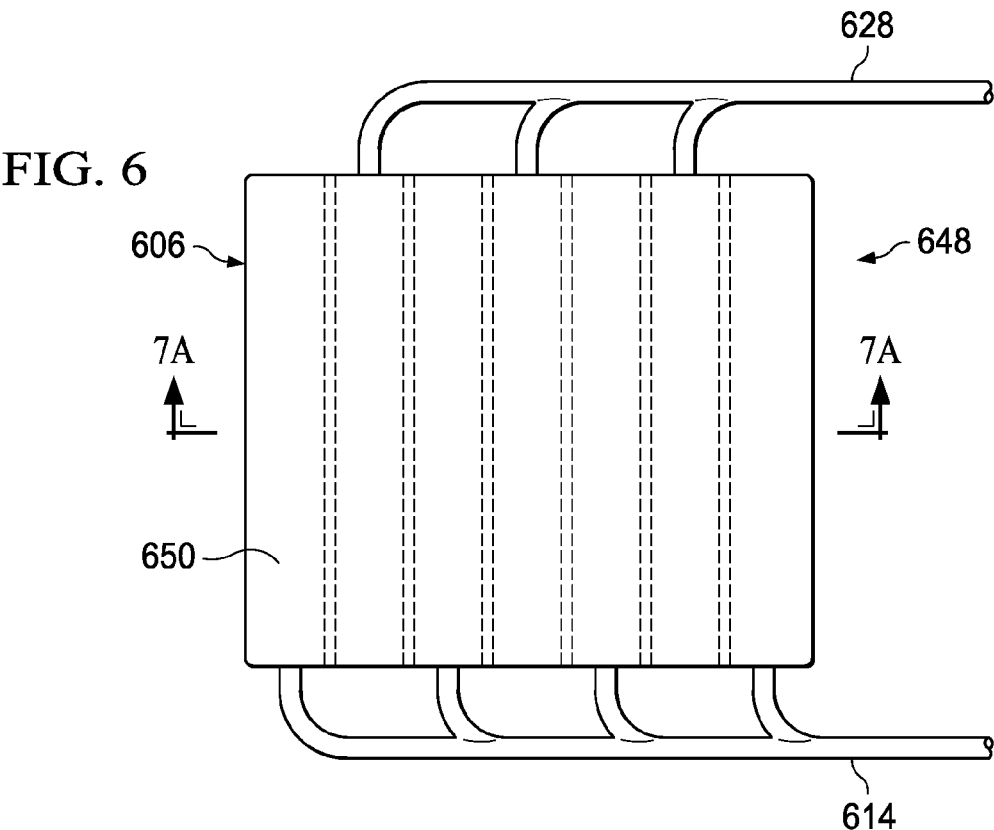
FIG. 6 is a schematic, top view of a planar structure having inflatable bladders and chambers between the inflatable bladders according to an illustrative embodiment.
Figure 7A:
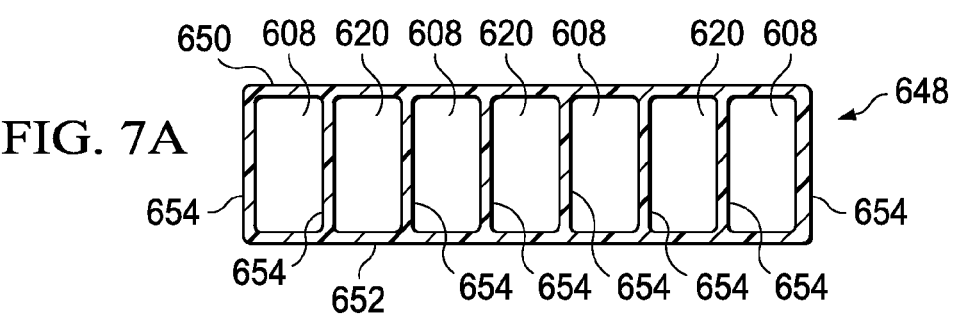
FIG. 7A is a schematic, cross-sectional view of the planar structure in FIG. 6 taken along line 7A-7A.
Figure 7B:
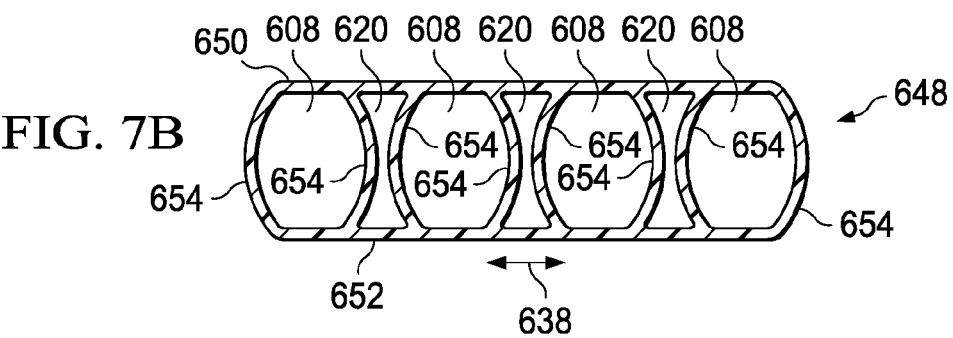
FIG. 7B is a schematic, cross-sectional view of the planar structure shown in FIG. 7A with inflatable bladders in the inflated position while reduced pressure is applied to the chambers located between the inflatable bladders.

Referring now to FIGS. 6, 7A and 7B, another illustrative embodiment of a multi-compartment dressing 606 is presented. The multi-compartment dressing 606 includes a planar structure 648 having inflatable bladders 608 and chambers 620. The planar structure 648 is formed from a top wall 650 and a bottom wall 652. The top wall 650 and the bottom wall 652 are joined together by a plurality of flexible side walls 654 that a plurality of compartments are formed that include inflatable bladders 608 and chambers 620. As shown in FIG. 7A, when the inflatable bladders 608 are in an un-inflated position and reduced pressure is not applied to the chambers 620, both the inflatable bladders 608 and the chambers 620 have substantially rectangular cross-sections. In other embodiments, however, the inflatable bladders 608 and the chambers 620 may have other cross-sectional shapes.

Fluid is supplied to the inflatable bladders 608 by a fluid supply conduit 614. Reduced pressure is supplied to the chambers 620 by a reduced-pressure conduit 628. The fluid supply conduit 614 and the reduced-pressure conduit 628 each have forked structures so that fluid and reduced pressure can be supplied to the individual inflatable bladders 608 and chambers 620. However, in other embodiments, only a single fluid supply conduit 614 and reduced-pressure conduit 628, each having non-forked structures, may be used or a plurality of individual conduits may be used. In the absence of such a forked conduit structure or individual conduits, the inflatable bladders 608 may be in fluid communication with one another and the chambers 620 may each be in fluid communication with one another. In this manner, reduced pressure supplied to a single chamber 620 may be transferred to the remaining chambers 620 in the planar structure 648. Likewise, fluid supplied to a single inflatable bladder 608 may be transferred to the remaining inflatable bladders 608.

FIG. 7A shows the inflatable bladders 608 in an un-inflated position due to an absence of fluid supply and also shows the chambers 620 in the absence of reduced pressure. In FIG. 7B, fluid has been supplied to the inflatable bladders 608 such that the inflatable bladders 608 are in an inflated position. In addition, reduced pressure has been applied to the chambers 620, thereby collapsing the chambers 620 and moving the inflatable bladders 608 closer to one another. The planar structure 648 has been compressed along the bidirectional arrow 638. Such compression can provide desirable compression forces upon a tissue site to enhance healing, as described above. In some instances, the planar structure 648 may be covered by a drape, such as drape 118 in FIG. 1. In an alternative embodiment, apertures may be formed on the bottom wall 652 to allow reduced pressure in chambers 620 to communicate with a tissue site Although the inflatable bladders 608 and the chambers 620 are shown to be substantially parallel to one another, the inflatable bladders 608 and the chambers 620 may have any orientation relative to one another and may have any shape. For example, either or both of the inflatable bladders 608 or chambers 620 may be concentric rings.

Figure 8:
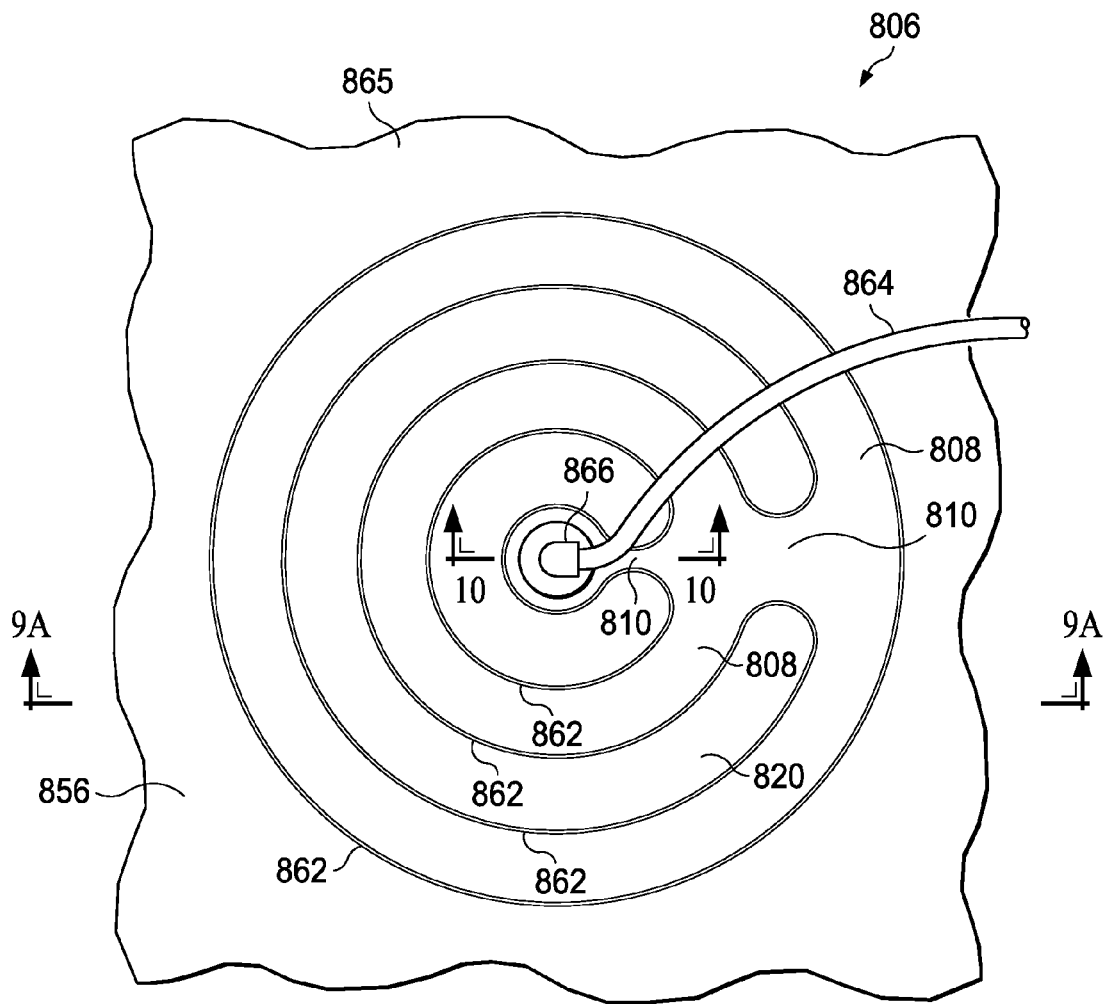
FIG. 8 is a schematic, top view of another illustrative embodiment of a dressing having inflatable bladders and chambers.
Figure 9A:
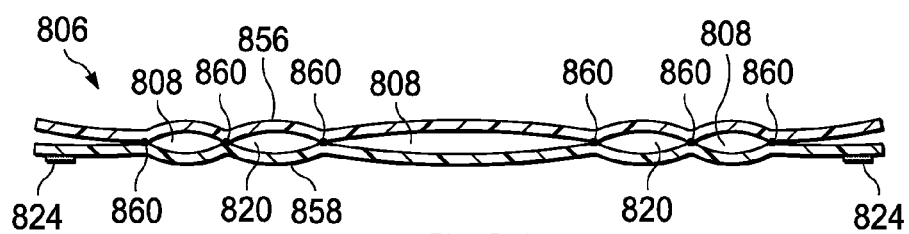
FIG. 9A is schematic, cross-sectional view of the dressing shown in FIG. 8 taken along line 9A-9A.
Figure 9B:
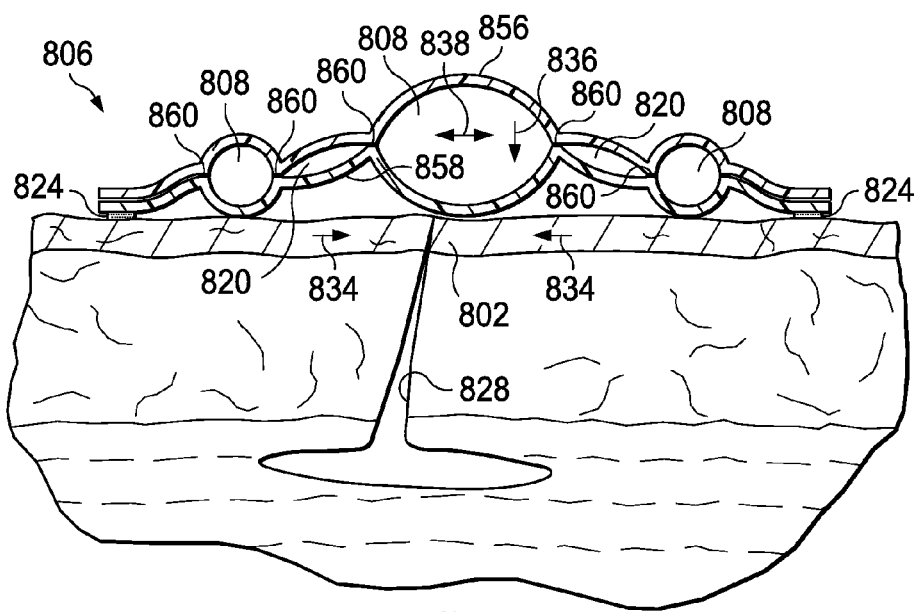
FIG. 9B is a schematic, cross-sectional view of the dressing shown in FIG. 9A with the inflatable bladders in the inflated position.
Figure 10:
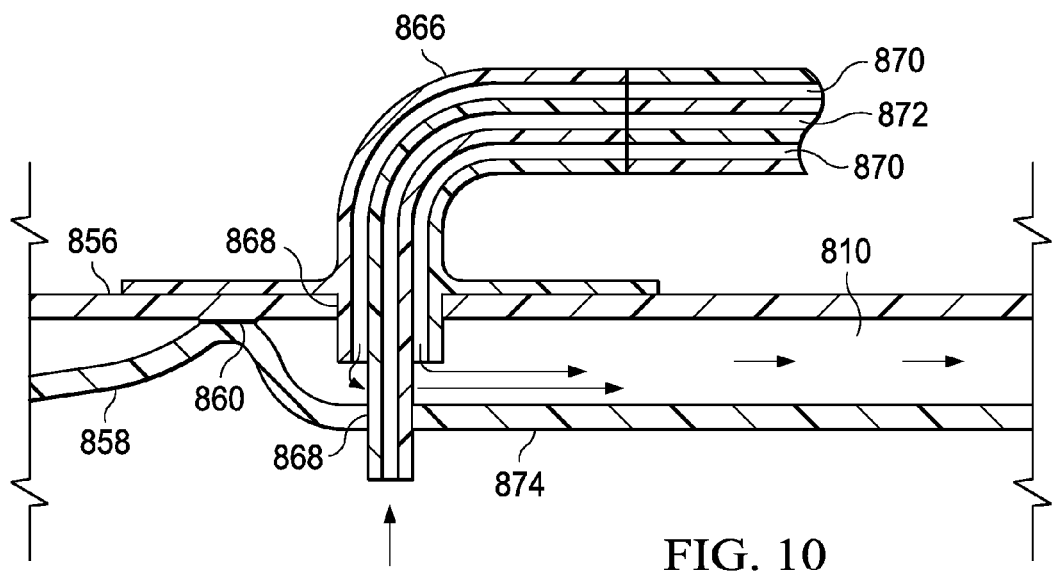
FIG. 10 is a schematic, cross-sectional view of the dressing shown in FIG. 8 taken along line 10-10.

Referring now to FIGS. 8 through 10, another embodiment of a dressing 806 is shown, which includes a first sheet 856 and a second sheet 858 that are coupled to one another at bonding sites 860 to form an inflatable bladder 808 and a chamber 820. While shown as a single inflatable bladder 808 and a single chamber in FIG. 8, it should be understood that multiple bladders and chambers may be formed as well. The first and second sheets 856, 858 may be made from any flexible material, including those materials described above from which the drape 118 in FIG. 1 may be formed. The first and second sheets 856, 858 are bonded to one another along lines 862, which generally define a border of the inflatable bladder 808 and the chamber 820. Fluid is prevented from flowing through the lines 862 and 863 by the bonds. To facilitate fluid impermeability along lines 862 and 863, the first sheet 856 may be bonded to the second sheet 858 using any known technique, including without limitation welding (e.g., ultrasonic or RF welding), bonding, adhesives, cements, etc.

The inflatable bladder 808 is in fluid communication with an interface 866 via a distribution conduit 810. In the dressing 806, the distribution conduit 810 is also formed by the configuration of the lines 862 at which the first and second sheets 856, 858 are bonded.

FIGS. 9A and 9B show the inflatable bladder 808 in an un-inflated position and an inflated position, respectively. Fluid is supplied to the inflatable bladder 808 by a conduit 864, for which additional detail will be provided below. The dressing 806 may be adhered to a tissue site 802 by an adhesive 824, which may be located at the periphery 865 of the dressing 806.

When fluid is supplied to the inflatable bladder 808, the inflatable bladder 808 expands into the inflated position, thereby moving the dressing 806 along the surface of the tissue site 802. The direction along which the dressing 806 moves when the inflatable bladders 808 are inflated is indicated by the bidirectional arrow 838. The contracting force along the bidirectional arrow 838 helps to cause an inward, or closing, force 834, which may be beneficial to the closing or healing of the wound 828. The adherence of the dressing 806 to the tissue site 802 by the adhesive 824 may also assist in providing or transmitting this inward force 834. Compression forces to the tissue site 802 along the arrow 836 may also be provided when the inflatable bladders 808 are in the inflated position.

In the embodiment represented by FIGS. 8 through 10, the chamber 820 is not subjected to reduced pressure to cause the collapse of the chambers 820. However, the chambers 820 do provide a spatial region along which the inflatable bladders 808 may move closer to one another when the inflatable bladders 808 are in an inflated position. In other embodiments, however, reduced pressure may be applied to the chamber 820. Moreover, in one embodiment, reduced pressure may be delivered to chamber 820 and apertures may be formed on the bottom of the dressing 806 that allow the reduced pressure in chamber 820 to be communicated to the tissue site 802.

Both fluid and reduced pressure may be supplied to the dressing 806 by a multi-lumen conduit 864, which is coupled to an interface 866. The interface 866 may be disposed in an aperture 868 that is through the first sheet 856 and the second sheet 858.

The multi-lumen conduit 864 includes at least a fluid lumen 870 and a reduced-pressure lumen 872. The interface 866 is structured to route the fluid transmitted through the fluid lumen 870 to the distribution conduit 810, which transmits the fluid to the inflatable bladder 808. The interface 866 is also structured to transmit reduced pressure from the reduced-pressure lumen 872 through the aperture 868 in the first and second sheets 856, 858 and to a tissue-facing side 874 of the dressing 806; in this manner, a fluid, including a gas, is drawn into the reduced-pressure lumen 872 from the tissue-facing side 874 of the dressing 806. Upon traveling through the dressing 806, the reduced pressure may be received by another structure, such as a bolster or manifold for a tissue site or wound. The multi-lumen structure of the conduit 864 and the routing function of the interface 866 allow reduced pressure and fluid to be supplied to the dressing 806 using a single multi-lumen conduit 864.

In other embodiments, reduced pressure may be supplied to the chamber 820 by the interface 866. Also, another conduit, such as a tube, may be inserted between the first sheet 856 and the second sheet 858 to transfer fluid from the interface 866 to the inflatable bladders 808. If such a conduit is used, the conduit may have perforations at those regions that are located within the inflatable bladders 808 so that conduit may be transferred thereto. The dressing 806 may also be used in conjunction with other parts described in the illustrative embodiments, such as the drape 118 in FIG. 1.

Although the present invention and its advantages have been disclosed in the context of certain illustrative, non-limiting embodiments, it should be understood that various changes, substitutions, permutations, and alterations can be made without departing from the scope of the invention as defined by the appended claims.

We claim:

1. A system for providing reduced-pressure treatment to a tissue site of a patient, the system comprising: a reduced-pressure source for supplying reduced pressure; a fluid source for supplying a fluid; a plurality of inflatable bladders for placing adjacent to the tissue site, the inflatable bladders operable to receive the fluid and to expand from an un-inflated position to an inflated position; and a plurality of chambers, the chambers being compressible; wherein at least one of the plurality of chambers is disposed between a first inflatable bladder and a second inflatable bladder of the plurality of inflatable bladders; wherein the inflatable bladders and the chambers are formed with a top wall, a bottom wall, and flexible side walls, and at least a portion of the flexible side walls partitions the inflatable bladders from the chambers; and the chambers are operable to receive the reduced pressure, the chambers are operable to collapse under reduced pressure and move the inflatable bladders closer to one another.

2. The system of claim 1, wherein the chambers compress when the inflatable bladders expand from the un-inflated position to the inflated position.

3. The system of claim 1, further comprising:
a drape for covering the inflatable bladders to form a sealed space when the inflatable bladders are placed proximate the patient's epidermis, the sealed space comprising the chambers; and
wherein the chambers are operable to receive the reduced pressure, the reduced pressure causing the chambers to collapse and move the inflatable bladders closer to one another.

4. The system of claim 1, further comprising:
a drape for covering the inflatable bladders to form a sealed space proximate the tissue site, the sealed space comprising the chambers; and
an adhesive for coupling a perimeter of the drape to the patient to facilitate sealing of the sealed space; and
wherein the chambers are operable to receive the reduced pressure and to collapse at least in part under reduced pressure.

5. The system of claim 1, wherein each of the inflatable bladders has a substantially rectangular cross-sectional shape when the inflatable bladder is in the un-inflated position, and the chambers each have a substantially rectangular cross-sectional shape in an absence of the reduced pressure.

6. A system for providing reduced-pressure treatment to a tissue site of a patient, the system comprising: a reduced-pressure source for supplying reduced pressure; a fluid source for supplying a fluid; a plurality of inflatable bladders for placing adjacent to the tissue site, the inflatable bladders operable to receive the fluid and to expand from an un-inflated position to an inflated position; and a plurality of chambers, the chambers being compressible; wherein at least one of the plurality of chambers is disposed between a first inflatable bladder and a second inflatable bladder of the plurality of inflatable bladders; a first sheet; a second sheet welded to the first sheet along weld lines to form the inflatable bladders, the chambers, and a distribution conduit, the distribution conduit providing fluid communication between the inflatable bladders.

7. The system of claim 1, wherein at least one of the inflatable bladders comprises:
a strut for limiting expansion of the at least one inflatable bladder along one direction when the at least one inflatable bladder is inflated.

8. The system of claim 1, further comprising:
a fluid conduit for providing fluid communication between the fluid source and the inflatable bladders; and
a fluid interface fluidly coupling the fluid conduit to the inflatable bladders.

9. The system of claim 1, further comprising:
a distribution conduit for providing fluid communication between the inflatable bladders.

10. The system of claim 1, further comprising:
a distribution conduit for providing fluid communication between the inflatable bladders, wherein the distribution conduit is corrugated to facilitate movement of the inflatable bladders.

11. An apparatus for providing reduced-pressure treatment to a tissue site of a patient, the apparatus comprising: a plurality of inflatable bladders for placing adjacent the tissue site, the inflatable bladders operable to receive a fluid and to expand from an un-inflated position to an inflated position; a plurality of chambers, the chambers being compressible; a distribution conduit, the distribution conduit providing fluid communication between the inflatable bladders; wherein at least one of the plurality of chambers is disposed between a first inflatable bladder and a second inflatable bladder of the plurality of inflatable bladders.

12. The apparatus of claim 11, wherein the chambers compress when the inflatable bladders expand from the un-inflated position to the inflated position.

13. The apparatus of claim 11, further comprising:
a drape for covering the inflatable bladders to form a plurality of sealed spaces proximate the patient, the sealed spaces comprising the chambers.

14. The apparatus of claim 11, further comprising:
a drape for covering the inflatable bladders to form a plurality of sealed spaces proximate the patient, the sealed spaces comprising the chambers;
a reduced-pressure conduit for transferring reduced pressure;
a reduced-pressure interface for fluidly coupling the reduced-pressure conduit and the plurality of sealed spaces; and
wherein the chambers are operable to receive the reduced pressure and to collapse and move the inflatable bladders closer to one another.

15. The apparatus of claim 11, further comprising:
a drape for covering the inflatable bladders to form a plurality of sealed spaces, the sealed spaces comprising the chambers;
an adhesive for coupling a perimeter of the drape to the patient to facilitate sealing of the sealed spaces; and
wherein the chambers are operable to receive reduced pressure and to collapse and move the inflatable bladders closer to one another.

16. The apparatus of claim 11, wherein:
the inflatable bladders and the chambers are formed with a top wall, a bottom wall, and flexible side walls; and
the chambers are operable to receive reduced pressure and to collapse thereby moving the inflatable bladders closer to one another.

17. The apparatus of claim 11, wherein:
the inflatable bladders and the chambers are formed from a top wall, a bottom wall, and flexible side walls;
the chambers are operable to receive reduced pressure and to collapse and move the inflatable bladders closer to one another; and
each of the inflatable bladders has a substantially rectangular cross-sectional shape when the inflatable bladder is in the un-inflated position, and the chambers each have a substantially rectangular cross-sectional shape in an absence of the reduced pressure.

18. The apparatus of claim 11, further comprising:
a first sheet; and
a second sheet coupled to the first sheet to form the inflatable bladders, the chambers, and a distribution conduit, the distribution conduit providing fluid communication between the inflatable bladders; and
wherein the chambers are operable to receive reduced pressure, and to collapse under reduced pressure and move the inflatable bladders closer to one another.

19. The apparatus of claim 11, wherein at least one of the inflatable bladders comprises:
a strut for limiting expansion of the at least one inflatable bladder along one direction when the at least one inflatable bladder is inflated.

20. The apparatus of claim 11, further comprising:
a distribution conduit for providing fluid communication between the inflatable bladders.

21. The apparatus of claim 11, wherein:
each of the inflatable bladders are substantially cylindrical when in the inflated position, and
the inflatable bladders are substantially parallel with one another.

22. The apparatus of claim 11, wherein the chambers are operable to receive a reduced pressure, the reduced pressure causing the chambers to collapse and move the inflatable bladders closer to one another such that a closing force is exerted upon a wound at the tissue site.

23. A method for providing reduced-pressure treatment to a tissue site of a patient, the method comprising: applying a multi-compartment dressing to the tissue site, the dressing comprising:
a plurality of inflatable bladders for placing adjacent to the tissue site, the inflatable bladders operable to receive a fluid and to expand from an un-inflated position to an inflated position, and a plurality of chambers, the chambers being compressible; wherein at least one of the plurality of chambers is disposed between a first inflatable bladder and a second inflatable bladder of the plurality of inflatable bladders; applying the fluid to the inflatable bladders to cause the inflatable bladders to expand into the inflated position; and applying a reduced pressure to the tissue site via the dressing.

24. The method of claim 23, wherein the chambers are compressed when the inflatable bladders expand to the inflated position.

25. The method of claim 23, further comprising:
applying the reduced pressure to the chambers to cause the chambers to collapse such that the inflatable bladders move closer to one another.

* * * * *